United States Patent
Gupta et al.

(10) Patent No.: US 8,363,791 B2
(45) Date of Patent: Jan. 29, 2013

(54) SYSTEM AND METHOD FOR COMMUNICATING MEDICAL ALERTS

(75) Inventors: Shekhar Gupta, Overland Park, KS (US); Rich Schermerhorn, Overland Park, KS (US); Victoria M. Toner, Sheboygan, WI (US); Johnny Hawkins, Kansas City, MO (US); Mike A. Roberts, Overland Park, KS (US)

(73) Assignee: CenturyLink Intellectual Property LLC, Denver, CO (US)

( * ) Notice: Subject to any disclaimer, the term of this patent is extended or adjusted under 35 U.S.C. 154(b) by 1099 days.

(21) Appl. No.: 12/119,256

(22) Filed: May 12, 2008

(65) Prior Publication Data

US 2008/0212746 A1  Sep. 4, 2008

Related U.S. Application Data (63) Continuation-in-part of application No. 11/607,186, filed on Dec. 1, 2006.

(51) Int. Cl.
*H04M 11/04* (2006.01)

(52) U.S. Cl. ......................................................... 379/38

(58) Field of Classification Search ..................... 379/38
See application file for complete search history.

(56) References Cited

U.S. PATENT DOCUMENTS

| | | | |
|---|---|---|---|
| 4,977,449 A | 12/1990 | Morgan | |
| 5,428,388 A | 6/1995 | von Bauer et al. | |
| 5,600,368 A | 2/1997 | Matthews, III | |
| 5,657,076 A | 8/1997 | Tapp | |
| 6,144,998 A | 11/2000 | Pisterzi | |
| 6,476,858 B1 | 11/2002 | Ramirez Diaz et al. | |
| 6,753,774 B2 | 6/2004 | Pan et al. | |
| 6,941,574 B1 | 9/2005 | Broadwin et al. | |
| 7,015,943 B2 | 3/2006 | Chiang | |
| 7,062,291 B2 | 6/2006 | Ryley et al. | |
| 7,109,860 B2 | 9/2006 | Wang | |
| 7,131,136 B2 | 10/2006 | Monroe | |
| 7,746,223 B2 | 6/2010 | Howarter et al. | |
| 7,839,446 B2 | 11/2010 | Hirano et al. | |
| 2002/0051059 A1 | 5/2002 | Shimizu et al. | |
| 2002/0075407 A1 | 6/2002 | Cohen-Solal | |
| 2003/0018975 A1 | 1/2003 | Stone | |
| 2003/0023974 A1 | 1/2003 | Dagtas et al. | |
| 2003/0123435 A1 | 7/2003 | Yeom et al. | |
| 2003/0135860 A1 | 7/2003 | Dureau | |
| 2003/0214930 A1 | 11/2003 | Fischer | |
| 2003/0227910 A1 | 12/2003 | Koyama | |
| 2004/0070620 A1 | 4/2004 | Fujisawa | |
| 2004/0086093 A1 | 5/2004 | Schranz | |
| 2004/0091089 A1 | 5/2004 | Wynn | |
| 2004/0153289 A1* | 8/2004 | Casey et al. .................. 702/188 |

(Continued)

OTHER PUBLICATIONS

Non-Final Rejection date mailed Feb. 10, 2009 in U.S. Appl. No. 11/607,526.

(Continued)

*Primary Examiner* — Alexander Jamal
(74) *Attorney, Agent, or Firm* — Swanson & Bratschun, L.L.C.

(57) ABSTRACT

A system and method for communication based on a condition of a user. A VoIP telephone is linked with a device for monitoring one or more health metrics of a user. The one or more health metrics of the user are received from the device. A speaker of the VoIP telephone is enabled to make a call in response to determining the one or more health metrics are not within a pre-defined rage. A receiving party is called in response to determining the one or more health metrics are not within a pre-defined range.

20 Claims, 6 Drawing Sheets

U.S. PATENT DOCUMENTS

| | | | |
|---|---|---|---|
| 2004/0155961 | A1 | 8/2004 | Litwin et al. |
| 2004/0233281 | A1 | 11/2004 | Tolmei |
| 2005/0063404 | A1 | 3/2005 | Karaoguz et al. |
| 2005/0080322 | A1* | 4/2005 | Korman .................. 600/300 |
| 2005/0111660 | A1 | 5/2005 | Hosoda |
| 2005/0132420 | A1 | 6/2005 | Howard et al. |
| 2005/0135570 | A1 | 6/2005 | Binning |
| 2005/0144024 | A1 | 6/2005 | Wojton et al. |
| 2006/0063517 | A1 | 3/2006 | Oh et al. |
| 2006/0174350 | A1 | 8/2006 | Roever et al. |
| 2006/0178138 | A1 | 8/2006 | Ostroff et al. |
| 2008/0022322 | A1 | 1/2008 | Grannan et al. |
| 2008/0030309 | A1 | 2/2008 | Darrouzet |
| 2008/0111684 | A1 | 5/2008 | Zinser |
| 2008/0120639 | A1 | 5/2008 | Walter et al. |
| 2008/0129498 | A1 | 6/2008 | Howarter et al. |
| 2008/0129821 | A1 | 6/2008 | Howarter et al. |
| 2009/0051767 | A1 | 2/2009 | Iwamura |
| 2009/0225750 | A1 | 9/2009 | Hawkins |

OTHER PUBLICATIONS

Response filed Mar. 3, 2009 to Non-Final Rejection dated Feb. 10, 2009 in U.S. Appl. No. 11/607,526.

Notice Regarding Non-Compliant/Non-Responsive Amendment dated mailed May 20, 2009 in U.S. Appl. No. 11/607,526.

Supplemental Response filed May 28, 2009 in U.S. Appl. No. 11/607,526.

Final Rejection date mailed Sep. 16, 2009 in U.S. Appl. No. 11/607,526.

Final Rejection and Examiner Interview Summary date mailed Nov. 17, 2009 in U.S. Appl. No. 11/607,526.

Response filed Feb. 1, 2010 to Final Rejection dated Nov. 17, 2009 in U.S. Appl. No. 11/607,526.

Terminal Disclaimer filed Feb. 10, 2010 in U.S. Appl. No. 11/607,526.

Notice of Allowance and Examiner Interview Summary date mailed Feb. 26, 2010 in U.S. Appl. No. 11/607,526.

Edward H. Frank et al., Connecting the home with a phone line network chip set, Pub. Year 2000; IEEE; 14 pages.

U.S. Appl. No. 11/607,186; Final Rejection dated Nov. 17, 2011; 34 pages.

U.S. Appl. No. 11/607,186; Non-Final Rejection dated Jun. 13, 2011; 25 pages.

U.S. Appl. No. 11/607,526; Issue Notification dated Jun. 9, 2010; 1 page.

U.S. Appl. No. 11/809,386; Final Rejection dated Apr. 11, 2012; 24 pages.

U.S. Appl. No. 12/044,792; Final Rejection dated Aug. 3, 2012; 33 pages.

U.S. Appl. No. 12/044,792; Non Final Office Action dated Mar. 2, 2012; 31 pages.

U.S. Appl. No. 12/044,792; Examiner Interview Summary dated Nov. 8, 2012; 12 pages.

U.S. Appl. No. 12/119,256; Non-Final Office Action dated Oct. 25, 2012; 51 pages.

\* cited by examiner

SYSTEM AND METHOD FOR COMMUNICATING MEDICAL ALERTS

CROSS-REFERENCE TO RELATED APPLICATIONS

This application is a continuation-in-part of U.S. patent application Ser. No. 11/607,186 filed Dec. 1, 2006, which is hereby incorporated by reference.

BACKGROUND

The use of and development of communications has grown nearly exponentially in recent years. The growth is fueled by larger networks with more reliable protocols and better communications hardware available to service providers and consumers. Users have similarly grown to expect better communications from home, work, and on the go. For example, users now expect faster connection speeds, increased bandwidth, better reliability, and greater availability from all types of communications networks. In many cases, the growth is driven by people looking to give up traditional communications schemes for the efficiency, effectiveness, and availability of new networks.

For example, options for communications with a phone have not significantly improved with changing technology. Most communications with family members at home, assisted living centers, and senior centers are limited to legacy systems, such as answering machines and speaker phones. Many individuals would warmly embrace technologies and features that enhance communication with aging parents and other family members to ensure well being, security, and peace of mind. There is a need for enhanced features for Voice over Internet Protocol (VoIP), standard telephones, wireless data and voice networks, and other communications devices, mediums, and networks.

SUMMARY

One embodiment provides a system and method for communication based on a condition of a user. A VoIP phone is linked with a device for monitoring one or more health metrics of a user. The one or more health metrics of the user are received from the device. A speaker of the VoIP phone is enabled to make a call in response to determining that the one or more health metrics are not within a pre-defined range. A receiving party is called in response to determining that the one or more health metrics are not within a pre-defined range.

Another embodiment provides a VoIP system. The VoIP system may include a wireless transceiver configured to communicate with one or more devices that measure one or more health metrics of a user. The wireless transceiver may receive the one or more health metrics. The VoIP system may include logic in communication with the wireless transceiver configured to determine whether the one or more health metrics exceed a threshold. The logic may call a receiving party associated with the threshold in response to the threshold being exceeded.

Yet another embodiment provides a VoIP phone. The VoIP phone may include a processing unit for processing a set of instructions and a memory configured to store the set of instructions. The set of instructions may be configured to link a VoIP phone with a device for monitoring one or more health metrics of a user, receive the one or more health metrics of the user from the device, enable a speaker of the VoIP phone to make a call in response to determining that the one or more health metrics are not within a pre-defined range, and call a receiving party based on a threshold met by the one or more health metrics, wherein the threshold indicates the receiving party to be called.

BRIEF DESCRIPTION OF THE DRAWINGS

Illustrative embodiments of the present invention are described in detail below with reference to the attached drawing figures, which are incorporated by reference herein and wherein.

DETAILED DESCRIPTION OF THE DRAWINGS

Illustrative embodiments provide a system and method for VoIP monitoring. The monitoring may be performed for aging parents, children or a specified location. The VoIP phone may be video-enabled. The VoIP phone is a telephonic device configured to send and receive voice communications, video, images, and other data through a network connection. The user may be required to receive an authorization or present a pass code that authorizes the user to monitor or carry on a two-way conversation with the VoIP phone remotely. As a result, the user may receive voice signals and/or video from the VoIP phone. Alternatively, the user may carry on an intercom or video conversation with a user that is unable to answer calls using traditional methods.

One or more VoIP phones or other communications devices may also be configured to send automated messages to one or more receiving parties. The automated messages may remind the receiving party to take medicine, feed the dog or perform other tasks. The automated message may require an acknowledgement, such as a voice command, gesture, facial recognition, number input or other information to acknowledge that the message was received and/or performed. For example, the message may determine whether an aging parent is doing well in an assisted living center. An automated call may play an audio file from the aging parent's child, such as "How are you doing mother?". No messages are sent if the parent responds "Good", "I am fine" or any other pre-programmed response. If, however, the aging parent responds "not well", "bad" or another response that is not an affirmative response, the VoIP phone may send a message, call or otherwise communicate to a user specified by user preferences. The VoIP phone may be configured to take any number of actions based on the affirmative or negative responses of the user.

Figure 1:
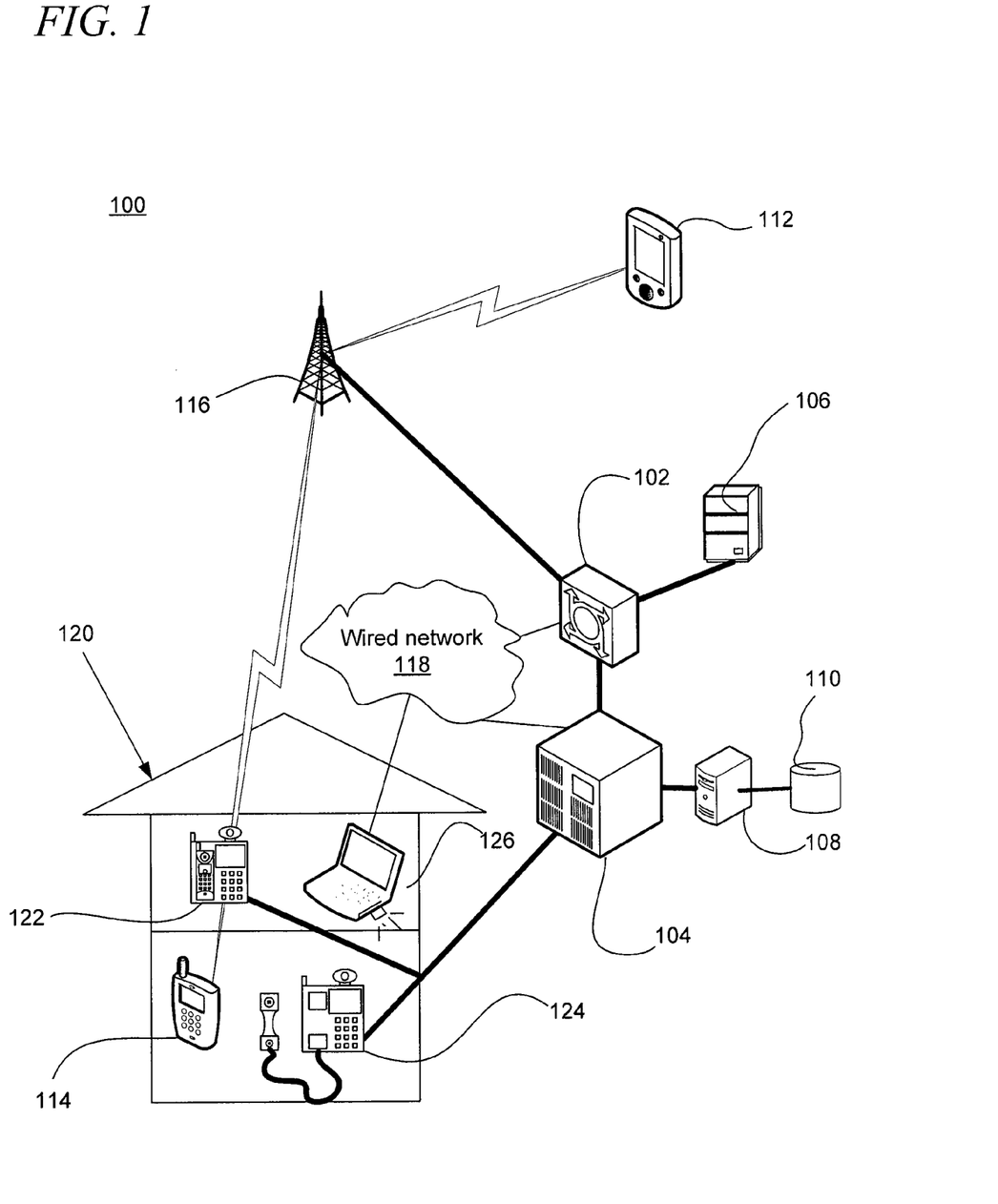
FIG. 1 is a perspective drawing of a communication system in accordance with an illustrative embodiment.

FIG. 1 is a pictorial representation of a communications system in accordance with an illustrative embodiment. The communication system 100 of FIG. 1 includes various elements used for wireless and wired communication including remote monitoring. The communications system 100 may include a mobile switching center (MSC) 102, a local exchange 104, voicemail systems 106 and 108, a database 110, wireless devices 112 and 114, a transmission tower 116, a wired network 118, a center 120, phones 122 and 124, and a client 126. In one embodiment, the different elements and components of the communications system 100 communicate using wireless communications including satellite connections or hardwired connections, such as fiber optics, T1, cable, DSL, high speed trunks, and telephone lines.

The wireless devices 112 and 114 may communicate with the transmission tower 116 using communications protocols, such as time division multiple access (TDMA), code division multiple access (CDMA), global systems for mobile (GSM) communications, personal communications systems (PCS), WLAN, WiMAX or other frequently used cellular, and data communications protocols and standards. The wireless devices 112 and 114 may include cellular phones, Blackberry®, personal digital assistances (PDA), mp3 players, laptops, evolution data optimized (EDO) cards, multi-mode devices, and other wireless communication devices and elements.

Communications within the communications system 100 may occur on any number of networks which may include wireless networks, data or packet networks, private networks, publicly switched telephone networks (PSTN), and the wired network 118. The networks of the communications system 100 may represent the hardware, software, and services of a single communication service provider or multiple communications services providers. The features of the embodiments may be implemented by one or more elements of the communications system 100 independently or as a networked implementation.

In one embodiment, the MSC 102, voicemail system 106, and transmission tower 116 are part of a wireless network that is operated by a wireless service provider. For example, the control signals and operational features may be performed by the MSC 102 and the wireless signals may be broadcast from the transmission tower 116 to the wireless devices 112 and 114. The wireless network may include any number of systems, towers, servers, and other network and communications devices for implementing the features and performing the methods herein described. For example, a user may monitor a VoIP phone from a cell phone enabled to send and receive live video.

The MSC 102 may be a switch used for wireless call control and processing. The MSC 102 may also serve as a point of access to the local exchange 104. The MSC 102 is a telephone exchange that provides circuit switched calling and mobility management and may also provide GSM or PCS services to the wireless devices 112 and 114 located within the area the MSC 102 serves. The MSC 102 may include a home location register (HLR) and visitor location register (VLR) that may be used to implement different features of the illustrative embodiments. The voicemail system 106 may be an integrated part of the MSC 102 or alternatively may be an externally connected device.

In one embodiment, the voicemail system 106 may include an integrated database for storing customer and usage information and data. The user may communicate, interact or send and receive data, information, and commands to the voicemail system 106 through the telephones 122 and 124, wireless devices 112 and 114, or the client 126. The MSC 102 and voicemail system 106 may include any number of hardware and software components.

The local exchange 104, the MSC 102, and/or other elements of the communications system 100 may communicate using a signal control protocol, such as a signaling system number 7 (SS7) protocol. The SS7 protocol is used in publicly switched networks for establishing connections between switches, performing out-of-band signaling in support of the call-establishment, billing, routing, and implementing information-exchange functions of the wired network 118. The local exchange 104 may be owned and operated by a local exchange carrier that provides standard telephone service to any number of users. In one embodiment, the local exchange 104 may be a class 5 switch that is part of the network systems of the local carrier. The local exchange 104 may include or may be connected to the voicemail system 106. However, the local exchange 104 may also be a Digital Subscriber Line Access Multiplexer (DSLAM), Internet Protocol (IP) gateway, base station or any other suitable network access point.

The local exchange 104 may be a wire-line switch or public exchange using time domain multiplexing to provide telecommunications services to a particular subscriber or groups of subscribers. The local exchange 104 may be located at a local telephone company's central office or at a business location serving as a private branch exchange. The local exchange 104 may provide dial-tone, calling features, and additional digital and data services to subscribers, such as home phones 122 and 124. In one embodiment, the local exchange 104 enables VoIP communication of the phones 122 and 124 through a data network. VoIP works by sending voice information in digital form, such as packets, rather than using the traditional circuit-committed protocols of the publicly switched network. The local exchange 104 may be or includes a feature server, a call control agent or an IP gateway for implementing VoIP communications.

The communications system 100 may further include any number of hardware and software elements that may not be shown in the example of FIG. 1. For example, in order to facilitate VoIP communications, the communications system and the MSC 102 and local exchange 104 in particular, may include additional application servers, media servers, service brokers, call agents, edge routers, gateways (signaling, trunking, access, sub, etc.), IP network service providers, adapters, exchanges, switches, users, and networks. The voicemail system 108 is similar to the voicemail system 106 except that it is equipped to handle voicemail for landline customers rather than wireless customers. The local exchange 104 or other components of a wire line network, such as data, PSTN, VoIP or other wired network may transfer the data and information utilized to perform the methods herein described.

The MSC 102 and the local exchange 104 may include an authentication space. The authentication space may be a partition, module or other storage or memory of the server designated by the communications service provider. The authentication space may validate that a user or device, such as client 126, is allowed to authorize the MSC 102, local exchange 104 or corresponding voicemail systems 106 and 108 to enable monitoring, set preferences, implement changes, configure automated messages and settings, review information or perform other updates. For example, a user may be first required to provide a secure identifier, such as a user name, password, pass code or other authentication code or hardware interface, to verify the user is authorized to make changes within the authentication space.

The authentication information may be used to create a secure connection between the client and the MSC 102 or the local exchange 104. The secure connection may be a virtual private network tunnel, an encrypted connection, firewall or other form of secured communications link. The MSC 102 and local exchange 104 may use any number of gateways, proxies, applications or interfaces for allowing the client 126 to the MSC 102 and local exchange 104 through the wired network 118. Alternatively, the client 126 may use a wireless network or other network to access the MSC 102 and local exchange 104. The MSC 102 and local exchange 104 may use a host client application for communicating with numerous clients.

The center 120 is an example of an assisted living facility, dwelling, nursing home, apartment, residence, senior center, business or location of a person or group that may utilize any number of communications services. The center 120 is shown as a residence in the illustrated example, however, the center 120 may also be an office, business or other structure wired or otherwise suitably equipped to provide telephone, data, and other communication services to one or more customers. In one embodiment, the center 120 is equipped with multiple communication devices, including phones 122 and 124, and client 126. The phones 122 and 124 may be standard devices that provide dialing and voice conversation capabilities. Phone 122 may be integrated in any number of other devices or may be used in different forms. For example, the phone 122 may be part of a refrigerator or intercom system. In another embodiment, the phone 124 may be integrated with a personal computer, such as client 126.

The communications services accessible from the phones 122 and 124 may include standard telephone service or VoIP phone service. The phones 122 and 124 may be VoIP phones or may be standard telephones that include a modem and/or VoIP adapters for enabling VoIP communications. In one embodiment, a special dial tone, message, web alert or other feedback may specify once or repeatedly that the phones 122 and 124 are going off-hook or performing monitoring. For example, the phones 122 and 124 may sound a double chirp when the video is automatically enabled for the phone 122. In another embodiment, the phones 122 and 124 give no indication that the monitoring is being performed. The phones 122 and 124 may be silent in order not to wake or disturb a person in the center 120 or in order to more securely determine the surroundings, settings, and security of the center 120 and any occupants. The user may cancel use of any features by reentering the feature command, hanging up or entering a cancellation command.

The client 126 may be a personal computer for performing and executing programs and instructions and accessing the wired network 118. However, the client 126 may be any computing devices suitable for communicating with the wired network 118 through a network connection. The wired network 118 may be a fiber optic, cable or telephone network or other wired network suitable for communication over a hard wired connection with the client 126. In one embodiment, the center 120 may include a wireless router, adapter, switch, hub or other suitable interface that allows the client 126 to communicate with the wired network 118. Alternatively, the client 126 may communicate with the wired network 118 through a wireless connection. The MSC 102 and local exchange 104 may use a graphical user interface (GUI), such as website or program accessible from the client 126 in order to enter and receive input preferences for performing the remote monitoring or setting automatic calling preferences.

In an illustrative embodiment, the user may provide user input, view content, make a video enhanced call or otherwise make selections and communicate commands using devices, such as or similar to, wireless devices 112 and 114, phones 122 and 124, and client 126.

At any time, a user may select to enable, order, initiate, configure, reconfigure, cancel or otherwise configure the way the remote monitoring is performed. For example, the user may use a command that informs a function trigger of a device or the device itself, such as the MSC 102, local exchange 104, voicemail systems 106 and 108, wireless devices 112 and 114, phones 122 and 124 or client 126, to begin remote monitoring. In one example, the user may submit a command to activate the remote monitoring by dialing *2 on the phone 122 and then entering a pass code, account code, password, pin number or other identifier. In another embodiment, a user may activate the feature by dialing *79 on the wireless device 112. The command may also be a password, voice activated, time activated, preset by user selection or any other suitable option, setting, command or user input. In another embodiment, the various features may be implemented using tactile commands.

Figure 2:
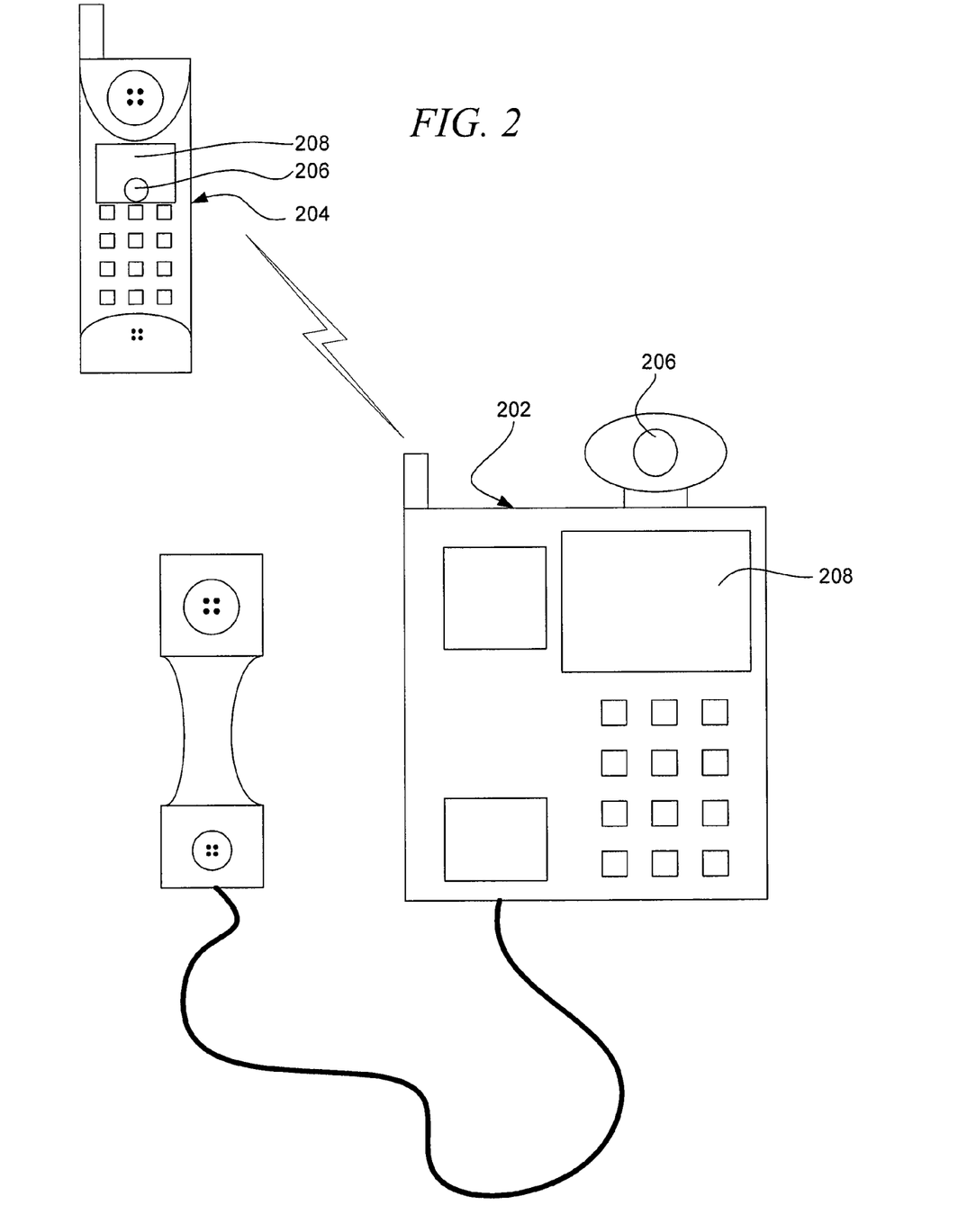
FIG. 2 is a perspective drawing of a video enabled VoIP system in accordance with an illustrative embodiment.

FIG. 2 shows examples of communications devices in accordance with an embodiment of the present invention. FIG. 2 includes a VoIP phone 202 and a cordless phone 204. The VoIP phone 202 and the cordless phone 204 may include a video camera 206 and a display 208, in addition to the standard hardware, software, and features.

The video camera 206 is a visual recording device. The video camera 206 may allow the VoIP phone 202 and the cordless phone 204 to record or stream live video images through a telephone or network connection of the VoIP phone 202. The display 208 is a graphical representation device. The display 208 may show text, video, images, graphics or other data and information. The VoIP phone 202 and cordless phone 204 may include any number of interface elements.

In one embodiment, the VoIP phone 202 and the cordless phone 204 may include a feature button. The feature button may be an interface that allows the user to send a signal or command to a class 5 switch, mobile switching center or voicemail system or other component of the communication system 100 of FIG. 1 to activate remote monitoring. Alternatively, the feature button may activate the individual device to perform the requested service.

The feature button may be a dedicated button, programmable or otherwise assignable graphical user interface, touch screen, microphone, scroll wheel or other input device that generates the command signal that activates the feature for the VoIP phone 202 and the cordless phone 204. The VoIP phone 202 and cordless phone 204 are particular implementations of the phones 122 or 124 of FIG. 1. The interfaces of the VoIP phone 202 and the cordless phone 204 may be utilized to activate any of the methods, services, and features herein described in addition to features available for standard VoIP phones and cordless phones.

The VoIP phone 202 and cordless phone 204 are telephonic devices that operate in conjunction with a data or packet network and/or VoIP network elements. The VoIP phone 202 and cordless phone 204 are provided dial tone connectivity through a data or network connection for a home, business or other location in which the VoIP phone 202 and cordless phone 204 are located. In another embodiment, the VoIP phone 202 may be a plain old telephone service (POTS) phone that functions using an analog connection.

In one embodiment, the VoIP phone 202 may operate as a cordless base station for the cordless phone 204. For example, the two devices may share a single phone number. The VoIP phone may establish a radio frequency link with the cordless phone 204 over a small distance, such as five hundred feet or less. The wireless frequency between the cordless phone 204 and VoIP phone 202 may be any frequency commonly used for short range communications including, but not limited to, 1.7 MHz, 27 MHz, 43-50 MHz, 900 MHz, 1.9 GHz, 2.4 GHz, 5.8 GHz, Bluetooth®, WiFi®. All voice, streaming video, data, and other information that are received during a phone call are channeled through the VoIP phone 202 to a user operating the cordless phone 204.

As a result, the VoIP phone 202 or the cordless phone 204 may be utilized to monitor or be remotely monitored. For example, a user may position the cordless phone 204 so that the phone may be automatically activated during a call to monitor one or more individuals in a room. For example, the cordless phone 204 may be positioned on a bedroom table to monitor a bed-ridden family member throughout the day. The VoIP phone 202 and the cordless phone 204 may be enabled to receive audio and visual feedback from a caller or receiving party. In particular, the VoIP phone 202 and the cordless phone 204 may recognize any number of responses including frames, actions, gestures or content received by the video camera 206. For example, the VoIP phone 202 and the cordless phone 204 may recognize responses which may include voice input, facial gestures, body position, motions, hand gestures or other feedback that a receiving party may be capable of performing.

Figure 3:
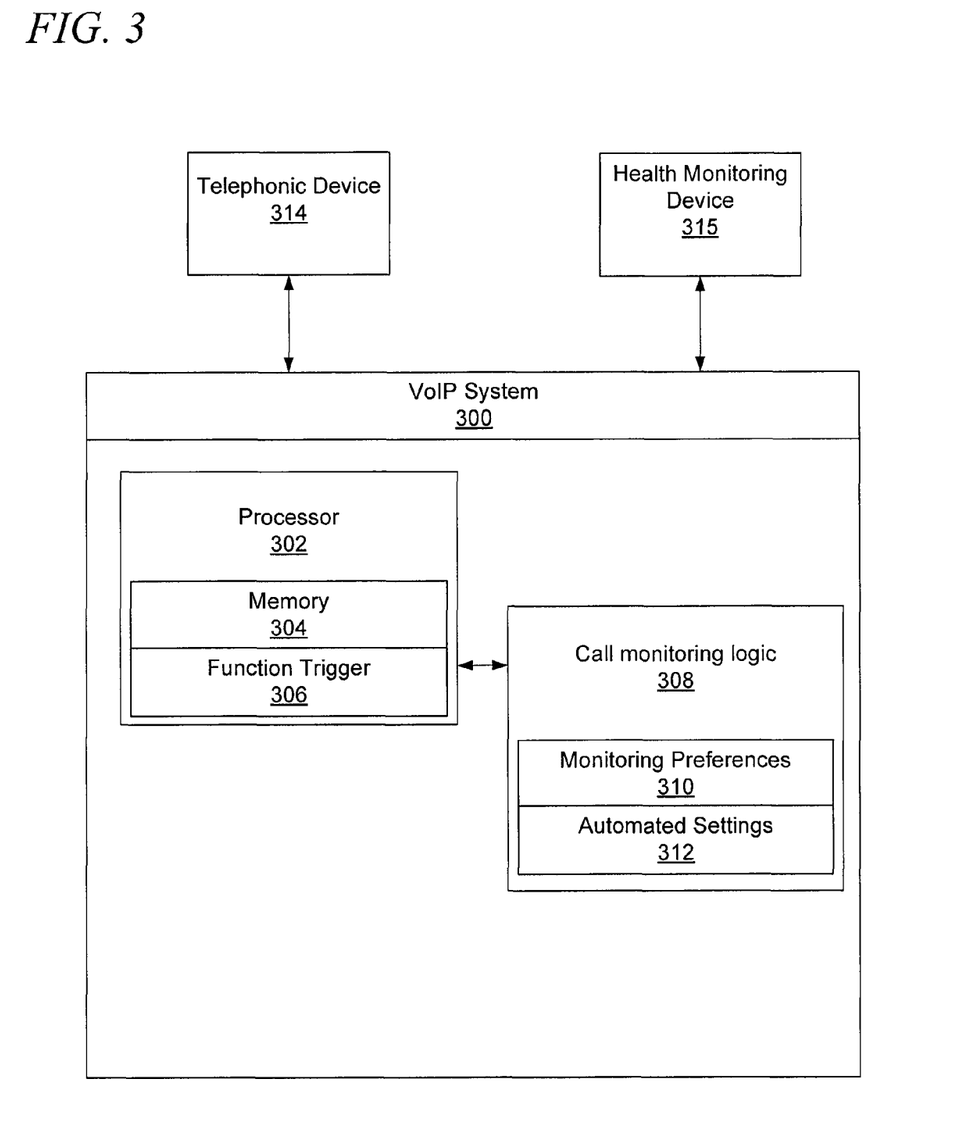
FIG. 3 is a block diagram of a home communication system in accordance with an illustrative embodiment.

FIG. 3 is a block diagram of a VoIP system in accordance with an illustrative embodiment. VoIP system 300 is a particular implementation of the VoIP phone 202 and/or cordless phone 204 of FIG. 2. The VoIP system 300 may be one or more telephonic devices, software modules and/or other devices configured to both make and receive a call for monitoring purposes.

In one embodiment, the VoIP system 300 includes a processor 302, a memory 304, a function trigger 306, call monitoring logic 308, monitoring preferences 310, and automated settings 312. The VoIP system 300 may communicate with a telephonic device 314. In one embodiment, the telephonic device 314 may be another VoIP phone which may include the elements of the VoIP system 300.

The processor 302, memory 304, function trigger 306, call monitoring logic 308, monitoring preferences 310, and automated settings 312 may be implemented individually or collectively in a single element, device or software component to provide the features herein described. The user input that is used by the function trigger 306 to enable the features described may be received directly by the VoIP system 300 through an interface, touch screen, buttons, dials or indicators or from the telephonic device 314 or other computing or communications devices.

The processor 302 is circuitry or logic enabled to control execution of a set of instructions. The processor 302 may be a microprocessor, digital signal processor, central processing unit or other device suitable for controlling an electronic device including one or more hardware and software elements, executing software, instructions, programs and applications, converting and processing signals and information, and performing other related tasks. The processor 302 may be a single chip or integrated with other computing or communications elements. The processor 302 may process voice signals which may include decoding and reassembling, as well as packetizing outgoing voice signals for transmission. The processor 302 may also execute a set of software modules to execute video monitoring.

The memory 304 is a hardware element, device or recording media configured to store data for subsequent retrieval or access at a later time. The memory 304 may be static or dynamic memory. The memory 304 may include a hard disk, random access memory, cache, removable media drive, mass storage or other storage suitable for recording data, instructions, and information. In one embodiment, the memory 304 and processor 302 may be integrated. The memory may use any type of volatile or non-volatile storage techniques and mediums. The VoIP system 300 or the memory 304 may include hardware or software for implementing voice commands and voice recognition. For example, utilizing voice recognition a user may access the VoIP system 300 or enter a message for delivery to any number of other VoIP devices.

In one embodiment, the function trigger 302 may be a software module triggered to implement monitoring using the VoIP system 300. The function trigger 302 activates the call monitoring logic 308 in response to receiving a pass code, password or other designated identifier. For example, after calling the VoIP system 300, a user may enter a code, such as *882 that the function trigger 306 receives and utilizes to activate the call monitoring logic 308.

In one embodiment, when an incoming call is received, the function trigger 306 may play a prompt to the calling party. This prompt may only be recognizable by the calling party for security purposes. Once the function trigger 306 has played the prompt or sent the prompt signal to the calling party, the function trigger 306 listens for a user selection. Once the function trigger receives the user selection, the function trigger prompts the calling party to enter a pass code. The pass code may be an identifier, password, authorization voice queue or other authentication message that ensures that the calling party is authorized to activate call monitoring or intercom communication. Next, the function trigger 306 determines whether the pass code is correct. If the pass code is correct, the function trigger 306 activates the call monitoring logic 308 based on the previous user selection.

In one embodiment, the memory 304 of the VoIP system 300 may allow a calling party to record the intercom conversation or monitored conversation. This may be particularly useful if there is a dramatic event occurring during the time the VoIP system 300 is being used to monitor a telephone, such as phones 122 and 124 of FIG. 1.

Call monitoring logic 308 is the digital logic, instructions, circuits or other elements that activate the VoIP system 300 to perform monitoring. The call monitoring logic 308 may be connected to a video camera, such as video camera 206 of FIG. 2, for streaming or recording video for transmission through a network connection. The call monitoring logic 308 may capture both audio and video content. The monitoring preferences 310 are the operational and procedural settings that define how and when the call monitoring logic 308 may be utilized. The monitoring preferences 310 may be established utilizing a user interface of the VoIP system 300 or externally through another device or interface. In one embodiment, the user may utilize a client device and a graphical user interface or a wireless device to set the preferences for the call monitoring logic 308.

The call monitoring logic 308 may be remotely or locally activated. For example, a child calling a parent at an assisted living facility may have previously agreed with the parent to enable the call monitoring logic 308 to be activated by the child remotely entering a pass code. As a result, the child is able to see how the parent is doing at any time without requiring user interaction of the parent.

In another embodiment, the call monitoring logic 308 may be configured to be activated only if the person called grants authorization through direct input, voice command, facial or bodily gesture or other programmed input. For example, a parent may grant authorization for the function trigger 306 to activate the call monitoring logic 308 by saying "video". The monitoring preferences 310 establish how and when the monitoring may be utilized. The receiving party may use a do-not-disturb feature to specify that incoming calls are not allowed to monitor the VoIP system 300 regardless of whether they have a pass code or not. In addition to storing remote access preferences, the monitoring preferences 310 may specify times of day that the call monitoring logic 308 may or may not be activated. In another example, a couple out on a date may be able to easily determine whether the babysitter has their children in bed for the night or determine whether the babysitter is still acting responsibly based on the streaming audio and video.

Additionally, the call monitoring logic 308 may be used to visually communicate with children, pets, disabled or handicapped family members or other individuals that are incapable of answering the VoIP system 300. For example, a wheelchair bound person may be able to speak, but may be unable to reach the phone. As a result, the call monitoring logic 308 may activate a video camera or a speaker function of the VoIP system 300 or a linked handset so that the calling party may communicate with the disabled person in the room without the disabled person being required to perform any tasks. The call monitoring logic 308 may be referred to as logic or an audio interface for implementing the monitoring communication described herein. The call monitoring logic 308 may establish whether an alert, prompt or indicator is played to the user indicating that the VoIP is off-hook in video and/or audio monitoring mode.

The automated settings 312 are instructions for automatically contacting one or more parties. As previously described, the VoIP system 300 may be the calling device that may communicate with an identical or different VoIP enabled-system. The automated settings 312 may include instructions for automatically contacting a party or for conveying a message. In one embodiment, the automated settings 312 may be configured to call a party at specified intervals. The call may request a desired input from the receiving party, such as a voice response, facial gesture or button input. In the event the desired input is not entered, another action may be taken. For example, the VoIP system 300 may be configured to call another VoIP phone in the room of an assisted living facility to check on a user's brother. The call monitoring logic 308 may call the user's brother every four hours during the day or twice a day and play a recorded audio message stating "How are you doing David?" If the user's brother provides a reply that is determined to be fine, the call ends. If, however, the user's brother does not respond or responds in the negative that he is not doing well, the VoIP system 300 may take further action. For example, the VoIP system 300 may send an email, text or video message. Alternatively, the VoIP system 300 may automatically call the user on a specified number or device and then link or bridge the calls so that the user may personally speak or attempt to speak with the user's brother.

The automated settings 312 may store pre-recorded messages or files that are to be played directly to the receiving party or that are to be converted to speech and then played. The automated settings 312 may also store potential responses of a receiving party and actions to take based on the type of response. For example, if no answer is received at the time the user calls, the VoIP system 300 may link with an intercom system of the center or facility and repeat the message or try back at specified intervals to determine the status of the receiving party. The automated settings 312 may store contact information which may include phone numbers, Internet Protocol (IP) addresses, account numbers, email addresses, user names, and other similar communications information.

In another embodiment, the automated settings 312 may be configured to retrieve, lookup or synchronize schedules, tasks, messages or other information from outside servers, devices or applications, such as Outlook, Goggle Calendar, and Microsoft Project Manager. For example, the user may enter a message and delivery times using a client device to be synchronized with the automated settings 312 of the VoIP system 300.

In one embodiment, the calling party may configure the automated settings 312 to call the receiving party three times a day at 9:00 a.m., 12:30 p.m., and 5:30 p.m. to remind the receiving party to take medications and to determine how the receiving party is responding to the medications. If the response indicates that the receiving party is not responding well, the automated settings 312 may be configured to send a text message to a wireless device of the calling party and bridge the call to the receiving party's doctor or pharmacist.

The call monitoring logic 308 may control other communications systems within the home. In one embodiment, the VoIP system 300 may be integrated with a specialized bed providing services to a disabled individual. The VoIP system 300 may also communicate with a home security system or media system. For example, the speakers and microphones of the home security system may be used to further monitor the home and perform intercom communication.

The call monitoring logic 308 may be configured to recognize voice input, motions, gestures or other input through a video camera or microphone of the VoIP system 300. The user and/or a receiving party may program a library of gestures, motions or other commands that are to be associated with a specified action. The call monitoring logic 308 may include an algorithm configured to search for and recognize the response and perform an associated action. For example, if the receiving party waves her hand in a specified manner, the call may be terminated. If, however, the user raises both fists, the call monitoring logic 308 may recognize that this image, subject matter or content as captured by the video camera indicates that the VoIP system 300 is to call 911 immediately and sound an alert. The call monitoring logic 308 may allow a user to pre-record a response in order to recognize responses utilizing comparison, video analysis, facial analysis or other similar searching or recognition logic.

Figure 4:
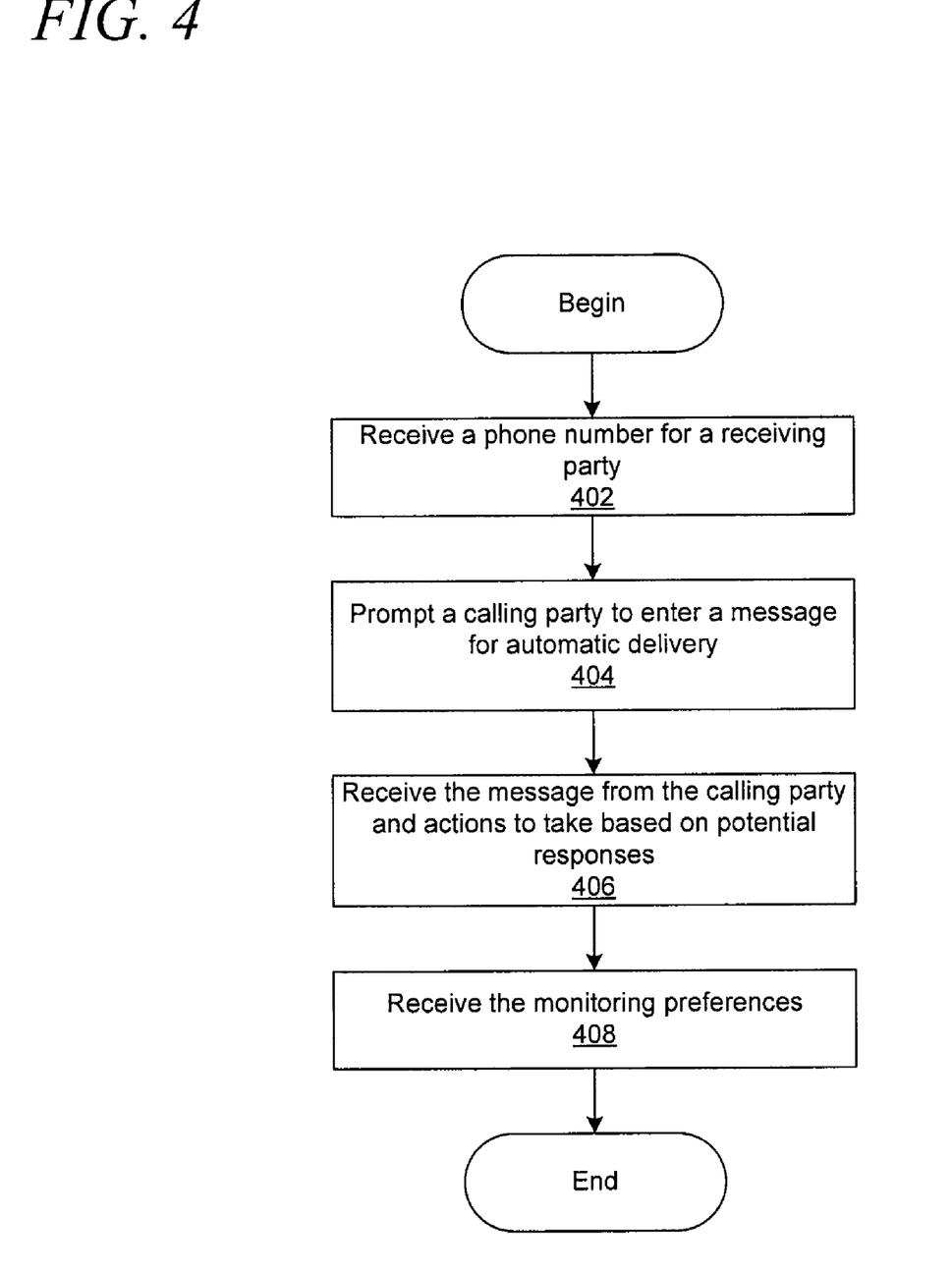
FIG. 4 is a flowchart of a process for remote monitoring in accordance with an illustrative embodiment.

FIG. 4 is a flowchart of a process for configuring messages for remote monitoring in accordance with an illustrative embodiment. The process of FIG. 4 may be implemented by one or more VoIP phones or systems. The process may begin by receiving a phone number for a receiving party (step 402). The receiving party may be the party the calling party is calling, such as a child or aging parent. The phone number may alternatively be an IP address, account number, nickname or other calling or communication information.

The VoIP phone prompts a calling party to enter a message for automatic delivery (step 404). The message may be any type of message for the receiving party. The message may also encompass a question, such as how are you doing today or have you taken your medicine yet today. The use of a message that provides comfort or an inquiry may be especially useful in the event that the user is unable to personally call the receiving party multiple times through out the day, week or month.

Next, the VoIP records the message from the calling party and receives actions to take based on potential responses (step 406). In one embodiment, the calling party may record the message using the VoIP phone. In another embodiment, the message may be imported, downloaded or otherwise received by the VoIP phone in the form of a file or other electronic media. The message may be an audio or video message recorded to make the message more personal. In another embodiment, the calling party may enter text that is converted to a voice message using text-to-speech applications utilized by the VoIP phone.

The calling party may also specify any number of expected or desired responses to the message in step 406. In one embodiment, the calling party may agree with the receiving party about potential responses and how they should be dealt with. For example, if the receiving party indicates that she is having a negative response to some new medications, a phone call may be bridged to a wireless device of the calling party and the receiving party's pharmacist.

The responses may also be recorded from the receiving party or the calling party. The response may be any number of actions that may be received or recorded by the VoIP phone. The responses may include voice responses, selections made utilizing the VoIP phone or a wireless device linked with the VoIP phone, bodily, motions or facial, gestures or other video-based responses. The response may be based on the physical abilities or capacity of the receiving party. For example, the receiving party may be temporarily incapacitated and only able to give responses by blinking. The VoIP phone may use a video camera to receive the blinking response and make a determination what the response means or how it is to be categorized for taking an action. In one embodiment, a library of potential responses may be linked with any number of actions.

The responses may then be linked with any number of actions that are to be taken by the VoIP phone. The actions may include sending additional text, voicemail, email or voice messages to a designated number or device, bridging a phone call, changing the interval of the call, engaging an intercom, activating an alarm or other networked system or reattempting the automated message. In some cases, there may be no response to the message because the user is away from the phone, sleeping, unconscious or otherwise unavailable. The actions may also indicate an action to take when no response is received, such as attempting the call and automated message again at a shortened interval of fifteen minutes instead of four hours.

Next, the VoIP phone receives monitoring preferences (step 408). The monitoring preferences may specify further details regarding how the call is made or implemented. For example, the monitoring preferences may specify whether the response is recorded, whether audio and video are available, and other elements for implementing the remote monitoring or automated message.

Figure 5:
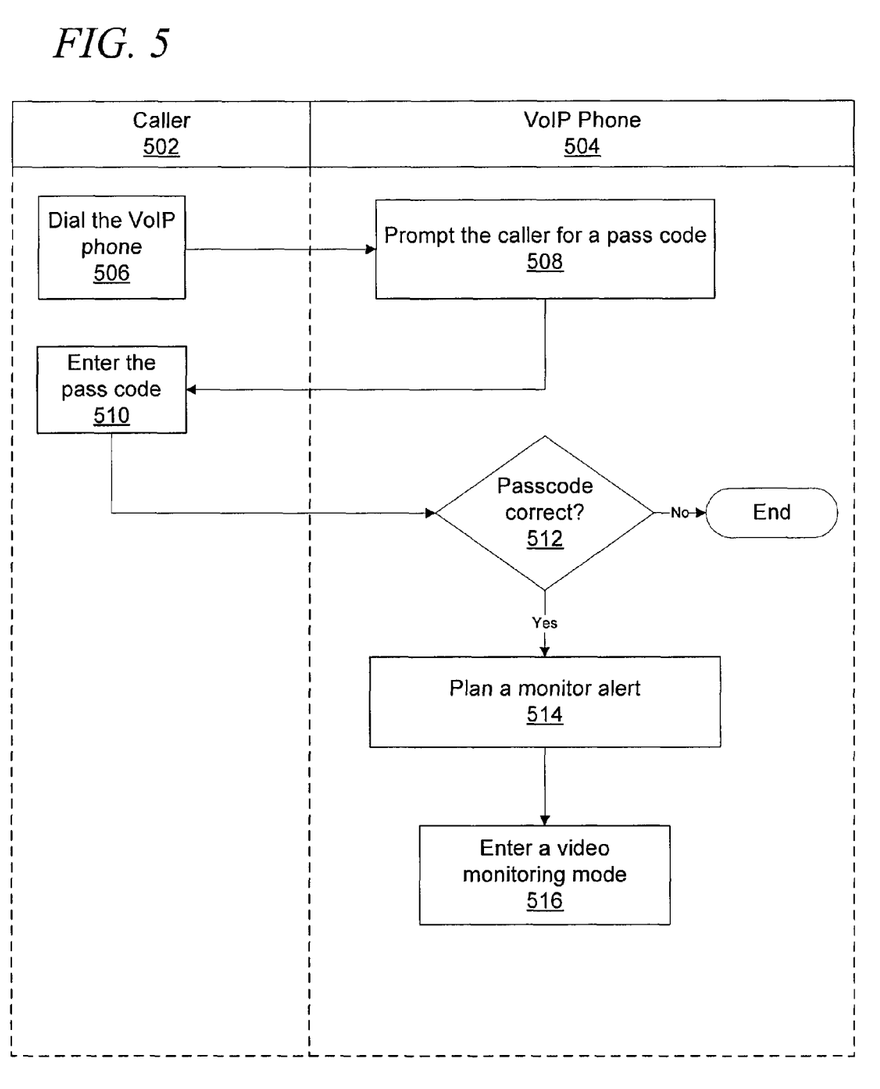
FIG. 5 is a flowchart of a process for home monitoring and using a home intercom in accordance with an illustrative embodiment.

FIG. 5 is a flowchart of a process for remote monitoring in accordance with an illustrative embodiment. The process of FIG. 5 describes a remote monitoring for a caller 502 and a VoIP phone 504. The caller 502 may be utilizing a VoIP system or phone to perform the monitoring as described in FIG. 5. Alternatively, the caller 502 may use any number of devices enabled for video communication.

The process begins with the caller 502 dialing a VoIP phone 504 (step 506). In another embodiment, a secondary VoIP phone may automatically call the VoIP phone 504 as a pre-programmed function or setting.

The VoIP phone 504 prompts the caller for a pass code (step 508). In one embodiment, during step 508, the VoIP phone 504 may play a prompt, alert or indicator that informs the caller 502 that remote monitoring may be available. The prompt of step 508 may be played or activated during the ring back period for allowing the caller 502 to enter a selection. In another embodiment, the VoIP phone 504 may not play a prompt in order to enhance security and the privacy of a receiving party utilizing the VoIP phone 504.

Next, the caller 502 enters the pass code (step 510). The pass code may be a button sequence, voice signal, command or other information that authorizes the caller 502 to perform a monitoring feature. Next, the VoIP phone 504 determines whether the pass code is correct (step 512). If the pass code is not correct, the process terminates. The pass code ensures that unauthorized parties are not able to monitor the home to avoid privacy and security issues.

If the pass code is correct in step 512, the VoIP phone 504 plays a monitor alert (step 514). The monitor alert may indicate to any individuals in the home that the phone is about to enter a monitor mode. The monitor alert may or may not be played based on the preferences, permissions or other authorizations of a receiving party.

Next, the VoIP phone 504 enters a video monitoring mode (step 516). During the video monitoring mode of step 516, the VoIP phone 504 may send and receive regular phone communications or video communications. The caller 502 may be enabled to see or hear anything within range of the VoIP phone 504. In another embodiment, the VoIP phone 504 may also communicate with a handset or other monitoring devices through a Bluetooth®, WiFi® or other wireless or wired connection. Monitoring may be terminated when the caller 502 enters user input to terminate the call.

In another embodiment, the pass code may be automatically entered by a VoIP device pre-programmed by the caller 502 to send an automated message. Once, the video monitoring mode is activated, the VoIP device may play an automated message to the VoIP phone 504. The automated message may be a comment, message of encouragement, information or an inquiry? In one example, the message asks how an elderly family member is doing. The response may be received by the VoIP phone 504 and transmitted back to the VoIP system or device. The response may be analyzed by the VoIP phone 504 or the VoIP device linked with the caller 502 to determine whether a pre-defined action linked with the response should be taken. For example, if a sequential blinking response indicates that the elderly family member in proximity to the VoIP is not doing well, the call may be linked or transferred to a registered work number utilized by the caller 502 so that the caller 502 may personally talk to the user. Alternatively, an email or text message may be sent to the caller 502 utilizing one or more alternative forms of communication.

Returning again to FIG. 3, the VoIP system 300 may also communicate with a health monitoring device 315. The health monitoring device 315 is a device or element configured to measure one or more health metrics for the user. The health metrics are vital measurements or other data or information about the patient's body. The health metrics may include temperature, pulse, blood pressure, breathing, blood sugar, irregular heartbeats, hormone levels, chemical levels or any other information that may be used to determine a condition or physical attribute of the user or patient.

The health monitoring device 315 may be a blood pressure monitor, pace maker or other similar device. The health monitoring device 315 may be worn by the user or may be attached, integrated or inserted within the user's body. In one embodiment, the health monitoring device 315 may be a blood pressure device that attaches to the user's wrist and subsequently determines a blood sugar level using a scanning device that measures glucose levels through the skin. The health monitoring device 315 may also include a device implanted in the user's hip in order to measure the user's pulse and potential blood infections in the user's blood stream.

The health monitoring device 315 may include any of the elements described for the VoIP system 300. In one embodiment, both the VoIP system 300 and the health monitoring device 315 may include a wireless transceiver. The wireless transceiver is a device configured to send and receive communications between the health monitoring device 315 and the VoIP system 300 wirelessly. As a result, the health monitoring device 315 may send the health metrics to the VoIP system 300 to be recorded, analyzed or otherwise processed. In one embodiment, the health monitoring device 315 may send an alert, alarm or other signal when a measured health metric is not within a predefined range. For example, if the user's heart beat exceeds 120 beats per minute, the health monitoring device 315 may send a signal to the VoIP system 300 informing the call monitoring logic 308 to enable a speaker system of the VoIP system 300 and call a receiving party. The receiving party may be a nurse, doctor, family member, friend or an automated emergency system or service, such as 911. The emergency service may include paramedics, firefighters, police, nurses, doctors or other medical professionals or consultants.

The health monitoring device 315 or the VoIP system 300 may store any number of thresholds or pre-defined ranges for measured health metrics that indicate whether a communication is to be initiated. The range may specify any one or more upper and lower thresholds for each health metric recorded by the health monitoring device 315. The range and thresholds may be specified by a medical professional, the user or other user with permissions or authority to access the VoIP system 300. In one embodiment, a combination of thresholds or circumstances may be linked with an alert or initiated call. For example, a call may only be initiated if the health monitoring device 315 determines the user's heart rate is above one hundred and twenty beats per minute while the user is lying down. The health monitoring device 315 may use any number of accelerometers or other sensors to measure movement or position of the user. Boolean logic within the health monitoring device 315 and VoIP system 300 may be utilized to determine whether a communication is to be initiated on behalf of the user.

The different thresholds of the range may also be linked with one or more communications options. For example, if the user's blood pressure exceeds a first level, the user's nurse may be called. If however, the user's blood pressure experiences a spike to a second level, the health monitoring device 315 or the VoIP system 300 may initiate a 911 call. Either the VoIP system 300 or the health monitoring device 315 may determine that the health metric is not within a pre-defined range and sends the health metrics to the receiving party as part of the call. For example, an emergency call or message to 911 based on a dropping pulse rate may include the user's name, address, condition, and the current health metrics of the user as read by the health monitoring device 315. As a result, even if the user is unable to communicate through the VoIP system 300 using a handset or a speaker phone function, the receiving party is still able to receive vital information in order to respond to the user's needs or circumstances. For example, the emergency information may be displayed to a screen or display of the emergency operator. In another example, the emergency information may be conveyed in an email, text, chat or other messaging format. If the user is capable, a voice response, indicator or other information provided by the user may indicate the person, organization, device or number to be called. The indicator may be a voice command, input through the VoIP system 300, a video response, tactile input or other user feedback. A default setting may specify one or more receiving parties to be called when there is no response from the user.

The VoIP system 300 may also communicate with any number of other VoIP systems, clients, terminals, computer, PDAs or wireless devices. For example, a doctor or relative of the user may access the VoIP system to determine the current health metrics being recorded and stored in the memory 304. The VoIP system 300 may also be configured to transmit measured health metrics periodically. The different elements of the VoIP system 300 may also allow a user to program how and when communications are initiated. The VoIP system 300 may require that a user have the appropriate permissions or provide a username, password or other authentication in order to configure the VoIP system 300.

In one embodiment, the call monitoring logic 308 may use a text-to-voice program to play an automated message during a call when the health metric exceeds the pre-defined range. The automated message may also be linked to one or more thresholds measured by the health monitoring device 315. For example, for a user that is unable to speak, an automated message may simply indicate that the user's glucose levels are approaching a range that indicates the user needs to receive an allotment of a prescribed drug from a doctor. In another embodiment, the call monitoring logic may also use a text-to-voice program to play a message to an emergency operator. For example, the message may specify the user's name, address, condition, and next of kin. In another embodiment, the user, a medical professional, relatives or friends may enter the information or text that is converted to a voice message.

The call monitoring logic 308 may also be used to record the health metrics as specified by the monitoring preferences 310. For example, the monitoring preferences 310 may indicate that the health metrics are to be stored in the memory 304 in a 24-hour loop. In another embodiment, the call monitoring logic 308 may initiate recording of the health metric streamed from the health monitoring device 315 in response to the health metrics leaving the pre-established range. In yet another embodiment, the call monitoring logic 308 may record the health metrics and the memory 304 at specified intervals as a reference or to be otherwise communicated to the receiving party. The illustrative embodiments may allow any number of individuals to review the user's health metrics before and after an event during which the health metric was not within the designated range.

The VoIP system 300 may also include a video camera or other visual recording devices. The visual recording device may also be activated by the call monitoring logic 308 in response to a health metric being above or below a specified range. For example, a video camera may be activated when the call monitoring logic 308 initiates a call to a sibling of the user so that the sibling may view the user to make a determination regarding the user's needs from other factors that may not be conveyed during a phone conversation, such as visible pain level or body position. In another example, the video camera may be activated by the call monitoring logic 308 so that a medical professional may view both the health metrics measured by the health monitoring device 315 as well as the user's appearance, body position, and other visually ascertainable information. The image may be used to diagnose and prepare to treat the user increasing the speed and efficiency of the response. The thresholds may be set at various warning levels so that the user may receive immediate treatment in order to avoid more dire emergency situations.

Figure 6:
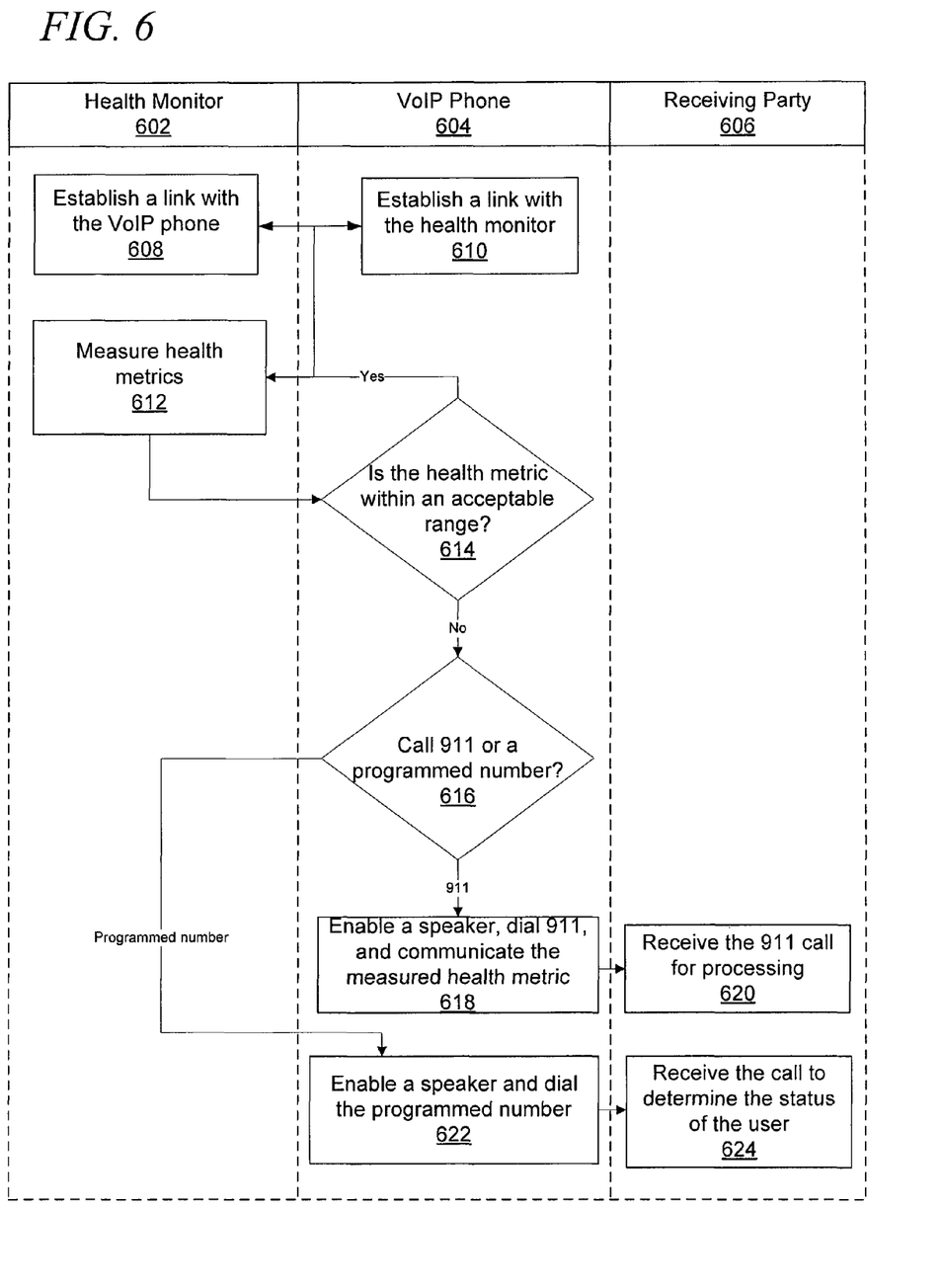
FIG. 6 is a flowchart of a process for initiating a call based on a health metric in accordance with an illustrative embodiment.

FIG. 6 is a flowchart of a process for initiating a call based on a health metric in accordance with an illustrative embodiment. The process of FIG. 6 may be implemented by a health monitor 602, a VoIP phone 604, and a receiving party 606. The health monitor 602 is a particular implementation of the health monitoring device 315 of FIG. 3. For example, the health monitoring device 602 may be a blood pressure monitor, pulse monitor, thermometer, blood sugar indicator or other similar device for measuring health metrics. The process of FIG. 6 may be initiated by the health monitor 602 establishing a link with the VoIP phone 604 (step 608). The VoIP phone 604 similarly establishes a link with the health monitor 602 (step 610). During steps 608 and 610, a wireless link between the health monitor 602 and the VoIP phone 604 may be established. The wireless connection may use a standard, such as, Bluetooth®, IEEE 802.11(n), infrared or other radio frequency standard, protocols or signals. In another embodiment, the health monitor 602 and the VoIP phone 604 may be connected together utilizing a hardwired connection. For example, a communications wire or cord may be attached from the health monitor 602 to the VoIP phone 604 in order to communicate information data and other signals.

Next, the health monitor 602 measures health metrics (step 612). The health monitor 602 may measure one or more health metrics of the user, such as, temperature, pulse, blood pressure, breathing, blood sugar, hormone levels, and other similar information. In one embodiment, the health monitor 602 may include one or more devices that are networked for integrated performance or function independently to communicate information to the VoIP phone 604.

Next, the VoIP phone 604 determines whether the health metric is within an acceptable range (step 614). The determination of step 614 may be made based on pre-specified information. For example, the user or medical personnel, family or other individuals may program the VoIP phone 604 or health monitor 602 with any number of ranges, thresholds, and actions to take based on those ranges or thresholds. For example, the user may indicate that a heart beat between 45 and 90 beats per minute is an acceptable range. If the heart beat drops below 45, the VoIP phone 604 may be programmed to dial 911. If the heart rate exceeds 90 beats per minute, the user's spouse may be called or a message may be communicated. Similarly, if the user's heart beat, as measured by the health monitor 602, exceeds 125 beats per minute, the VoIP phone 604 may be programmed to dial 911. The determination of step 614 may also be made by the health monitor. If the health monitor determines the health metric is not within the designated range, the health monitor 602 may send a control signal or command to the VoIP phone 604 to initiate a call to 911 or one or more other programmed numbers. If the health metric is within an acceptable range in step 614, the health monitor 602 continues to measure health metrics (step 612).

If the health metric is not within an acceptable range in step 614, the VoIP phone 604 determines whether to call 911 or a programmed number (step 616). The determination of step 616 may be made based on multiple thresholds and actions linked with the thresholds. In one embodiment, a lower threshold or less serious event may be utilized to call a parent of the user, while a higher threshold or more serious event as determined by the measured health metrics, may be used to call 911 or another emergency service.

If the VoIP phone 604 determines to call 911, the VoIP phone 604 enables the speaker, dials 911, and communicates the measured health metric (step 618). A speaker function of the VoIP phone 604 may be enabled when the call is dialed during step 618 so that the user may directly provide the 911 operator or other emergency personnel information or feedback regarding his or her circumstances or health.

The receiving party 606 receives the 911 call for processing (step 620). At this point, the receiving party 606 may communicate with the VoIP phone 604 and corresponding user in order to determine what services, attention or assistance the user may need. In one embodiment, the relevant health metrics or other emergency information may be transmitted from the VoIP phone 604 to the receiving party 606. The emergency information may include the user's address, contacts, medical history or situation, current and past health metrics, and current images as recorded by a video camera in addition to other details and information that may useful.

The emergency information may be particularly useful if the user is unable to utilize the speaker function of the VoIP phone 604 to communicate with emergency personnel. If the VoIP phone 604 determines to call a programmed number in step 616, the VoIP phone 604 enables the speaker and dials the program number (step 622). The programmed number may be indicated or programmed by the user or other person assisting the user. The number may alternatively be an Internet Protocol address, account number, username or other similar information for initiating a communication or sending a message. In one embodiment, each day the user may press a soft key or button of the VoIP phone 604 in order to program the number that is to be called based on certain thresholds of health metrics. For example, a low blood sugar level that may be used to indicate diabetic shock may be linked with a phone number of the user's friend that may live close by.

The programmed number may include any number of alternates in case the receiving party 606 does not answer, the line is busy or an answering machine picks up. As a result, the VoIP phone 604 may cycle through any number of phone numbers until one or more of the receiving parties answer the phone. Once the receiving party 606 answers the call, the speaker phone is enabled in order to allow the user to carry-on a conversation or otherwise communication with the receiving party 606. In another embodiment, the speaker phone may be enabled in order to receive a verbal command from the user specifying the receiving party 606 to be called.

Similarly the VoIP phone 604 may use a video camera to stream images to the receiving party 606. The receiving party 606 receives the call to determine the status of the user (step 624). For example, based on the phone call, the receiving party 606 may visit the user, call a medical professional or otherwise provide assistance, assurance or comfort as needed by the user.

The features of the present invention may be used independently or in combination to provide improved communications options and security for a user from a VoIP phone or other similar communications device. The features and services herein described may be implemented as a baby monitor, to monitor remote properties or for other similar uses or purposes. The previous detailed description is of a small number of embodiments for implementing the invention and is not intended to be limiting in scope. The following claims set forth a number of the embodiments of the invention disclosed with greater particularity.

What is claimed:

1. A method for communication based on a condition of a user, the method comprising:
   linking a voice over internet protocol (VoIP) telephone with a device for monitoring one or more health metrics of a user;
   receiving the one or more health metrics of the user from the device;
   recognizing, in response to determining the one or more health metrics are not within a pre-defined range, a receiving party associated with a range covering one of the received one or more health metrics, and wherein different ranges for the one or more health metrics are linked with different receiving parties;
   calling the receiving party; and
   enabling a speaker of the VoIP telephone to allow the user to participate in the call in response to calling the receiving party.

2. The method according to claim 1, wherein the calling further comprises:
   receiving a voice command from the user through a microphone for the VoIP telephone to dial the receiving party.

3. The method according to claim 1, further comprising:
   displaying the one or more health metrics to the receiving party during the call.

4. The method according to claim 1, further comprising:
receiving communication information for calling the receiving party.

5. The method according to claim 1, wherein the calling is performed in response to the user not giving an indicator.

6. The method according to claim 1, further comprising:
recording the one or more health metrics;
sending a recording of the one or more health metrics with the call.

7. The method according to claim 1, further comprising:
enabling a camera for streaming an image of the user to the receiving party in response to calling the receiving party.

8. The method according to claim 1, wherein the calling further comprises:
automatically dialing an emergency service.

9. The method according to claim 1, further comprising:
receiving a number associated with the receiving party before receiving the health metrics.

10. The method according to claim 1, wherein the VoIP telephone and the device communicate through a wireless connection.

11. The method according to claim 1, the pre-defined range further comprising a plurality of thresholds, each of the plurality of thresholds is associated with one or more receiving parties that are called based on the one or more health metrics exceeding one of the associated plurality of thresholds.

12. The method according to claim 11, wherein the device determines which of the plurality of thresholds is met by the one or more health metrics, and wherein the device sends a control signal to the VoIP telephone specifying a phone number for the receiving party.

13. The method according to claim 1, further comprising:
communicating emergency information regarding the user to be displayed by a communications device of the receiving party.

14. A VoIP system, the system comprising:
a wireless transceiver configured to communicate with one or more devices that measure one or more health metrics of a user, the wireless transceiver receives the one or more health metrics; and
logic in communication with the wireless transceiver configured to determine whether the one or more health metrics exceed a threshold, wherein the logic recognizes, in response to determining the received one or more health metrics are not within a pre-defined range, a receiving party associated with a range covering one of the received one or more health metrics, and the logic calls the receiving party, wherein different ranges for the one or more health metrics are linked with different receiving parties.

15. The VoIP system according to claim 14, further comprising:
a memory configured to record the one or more health metrics for transmission to the receiving party.

16. The VoIP system according to claim 14, further comprising:
a video camera configured to stream an image to the receiving party for determining a condition of the user in response to a call being initiated by the logic.

17. The VoIP system according to claim 14, wherein the logic is configured to automatically dial an emergency service as the receiving party in response to not receiving an indicator from the user.

18. A VoIP phone comprising:
a processing unit for processing a set of instructions; and
a memory configured to store the set of instructions, wherein the set of instructions is configured to:
link a voice over internet protocol (VoIP) telephone with a device for monitoring one or more health metrics of a user;
receive the one or more health metrics of the user from the device;
recognize, in response to determining the received one or more health metrics are not within a pre-defined range, a receiving party associated with a range covering one of the received one or more health metrics, and wherein different ranges for the one or more health metrics are linked with different receiving parties;
call the receiving party; and
enable a speaker of the VoIP telephone to allow a user to participate in the call in response to calling the receiving party.

19. The VoIP phone according to claim 18, wherein the set of instructions further:
communicates emergency information regarding the user to be displayed by a communications device of the receiving party, and wherein the emergency information includes a name of the user, address, medical conditions, and recordings of the one or more health metrics.

20. The VoIP phone according to claim 18, wherein the set of instructions further:
enables a camera for streaming an image of the user to the receiving party in response to calling the receiving party.

* * * * *